United States Patent
Wijay

(10) Patent No.: US 6,340,366 B2
(45) Date of Patent: *Jan. 22, 2002

(54) STENT WITH NESTED OR OVERLAPPING RINGS

(76) Inventor: Bandula Wijay, 1903 Carriage Creek Dr., Friendswood, TX (US) 77546

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/207,867
(22) Filed: Dec. 8, 1998
(51) Int. Cl.⁷ .................................................. A61F 2/06
(52) U.S. Cl. ....................................... 623/1.13; 623/1.15
(58) Field of Search ................................ 606/198, 191, 606/192, 195–197, 108; 623/1, 1.15, 1.17, 1.22, 1.3, 1.13

(56) References Cited

U.S. PATENT DOCUMENTS

| | | |
|---|---|---|
| 4,503,569 A | 3/1985 | Dotter |
| 4,580,568 A | 4/1986 | Gianturco |
| 4,732,152 A | 3/1988 | Wallsten et al. |
| 4,740,207 A | 4/1988 | Kreamer |
| 4,776,337 A | 10/1988 | Palmaz |
| 4,795,458 A | 1/1989 | Regan |
| 4,820,298 A | 4/1989 | Leveen et al. |
| 4,886,062 A | 12/1989 | Wiktor |
| 4,913,141 A | 4/1990 | Hillstead |
| 4,950,227 A | 8/1990 | Savin et al. |
| 4,964,853 A | 10/1990 | Sugiyama et al. |
| 4,969,458 A | 11/1990 | Wiktor |
| 4,990,151 A | 2/1991 | Wallsten |
| 5,015,253 A | 5/1991 | MacGregor |
| 5,019,090 A | 5/1991 | Pinchuk |
| 5,041,126 A | 8/1991 | Gianturco |
| 5,100,429 A | 3/1992 | Sinofusky et al. |

(List continued on next page.)

FOREIGN PATENT DOCUMENTS

| | | |
|---|---|---|
| EP | 421729 A2 | 4/1991 |
| EP | 540290 A2 | 5/1993 |
| EP | 556850 A1 | 8/1993 |
| EP | 621017 A1 | 10/1994 |
| EP | 662307 A1 | 7/1995 |
| FR | 2671280 A1 | 7/1992 |
| FR | 2702954 A1 | 9/1994 |
| WO | WO 91/12047 | 8/1991 |
| WO | WO 92/11824 | 7/1992 |
| WO | WO 92/16166 | 10/1992 |
| WO | WO 94/20044 | 9/1994 |
| WO | WO 95/03010 | 2/1995 |

OTHER PUBLICATIONS

AngioStent Balloon Expandable Stent System, AngioDynamics Division of E–Z–EM, Inc., Sep., 1994.

Gianturco–Roubin Flex–Stent Coronary Stents, Cook Cardiology, 1995 (brochure).

Medtronic WIKTOR GX, Medtronic Interventional Vascular, no date (brochure).

Miscellaneous literature regarding PS stent, no date.

Miscellaneous literature regarding stent, no date.

Miscellaneous literature regarding Wikor Stents, no date.

Miscellaneous literature regarding Wallstent, no date.

Donald S. Daim, MD, "New Stent Designs," 2 pages, dated after Aug. 1995.

*Primary Examiner*—Michael H. Thaler
(74) *Attorney, Agent, or Firm*—Steve Rosenblatt

(57) ABSTRACT

A flexible stent is disclosed which reduced openings between rings by two alternative techniques. In the first instance, adjacent sinusoidally bending rings are nested to compact them closer together to reduce the opening sizes therebetween. In another embodiment, adjacent sinusoidal rings overlap each other to achieve the same effect. The assembly can be covered with a graft as a support therefor.

8 Claims, 10 Drawing Sheets

U.S. PATENT DOCUMENTS

| | | |
|---|---|---|
| 5,108,416 A | 4/1992 | Ryan et al. |
| 5,133,732 A | 7/1992 | Wiktor |
| RE34,037 E | 8/1992 | Innue et al. |
| 5,139,480 A | 8/1992 | Hickle et al. |
| 5,158,548 A | 10/1992 | Lau et al. |
| 5,160,341 A | 11/1992 | Brenneman et al. |
| 5,163,951 A | 11/1992 | Pinchuk et al. |
| 5,163,952 A | 11/1992 | Froix |
| 5,163,958 A | 11/1992 | Pinchuk |
| 5,183,085 A | 2/1993 | Timmermans |
| 5,195,984 A | 3/1993 | Schatz |
| 5,197,978 A | 3/1993 | Hess |
| 5,213,561 A | 5/1993 | Weinstein et al. |
| 5,222,969 A | 6/1993 | Gillis |
| 5,222,971 A | 6/1993 | Willard et al. |
| 5,234,457 A | 8/1993 | Andersen |
| 5,236,447 A | 8/1993 | Kubo et al. |
| 5,258,042 A | 11/1993 | Mehta |
| 5,266,073 A | 11/1993 | Wall |
| 5,282,823 A | 2/1994 | Schwartz et al. |
| 5,282,824 A | 2/1994 | Gianturco |
| 5,287,861 A | 2/1994 | Wilk |
| 5,292,331 A | 3/1994 | Boneau |
| 5,304,121 A | 4/1994 | Sahatjian |
| 5,304,200 A | 4/1994 | Spaulding |
| 5,306,294 A | 4/1994 | Winston et al. |
| 5,314,472 A | 5/1994 | Fontaine |
| 5,334,201 A | 8/1994 | Cowan |
| 5,336,518 A | 8/1994 | Narayanan et al. |
| 5,342,348 A | 8/1994 | Kaplan |
| 5,344,426 A | 9/1994 | Lau et al. |
| 5,354,308 A | 10/1994 | Simon et al. |
| 5,354,309 A | 10/1994 | Schnepp-Pesch et al. |
| 5,360,401 A | 11/1994 | Turnland |
| 5,368,566 A | 11/1994 | Crocker |
| 5,370,683 A * | 12/1994 | Fontaine |
| 5,370,691 A | 12/1994 | Samson |
| 5,383,928 A | 1/1995 | Scott et al. |
| 5,389,106 A | 2/1995 | Tower |
| 5,391,172 A | 2/1995 | Williams et al. |
| 5,397,355 A | 3/1995 | Marin et al. |
| 5,403,341 A | 4/1995 | Solar |
| 5,405,377 A | 4/1995 | Cragg |
| 5,421,955 A | 6/1995 | Lau et al. |
| 5,423,885 A | 6/1995 | Williams |
| 5,433,706 A | 7/1995 | Abiuso |
| 5,437,632 A | 8/1995 | Engleson |
| 5,439,444 A | 8/1995 | Anderson et al. |
| 5,439,445 A | 8/1995 | Kontos |
| 5,441,515 A | 8/1995 | Khosravi et al. |
| 5,443,496 A | 8/1995 | Schwartz et al. |
| 5,443,500 A | 8/1995 | Sigwart |
| 5,449,373 A | 9/1995 | Pinchasik et al. |
| 5,480,423 A | 1/1996 | Ravenscroft et al. |
| 5,496,365 A | 3/1996 | Sgro |
| 5,507,767 A | 4/1996 | Maeda et al. |
| 5,527,354 A | 6/1996 | Fontaine et al. |
| 5,540,712 A | 7/1996 | Kleshinski et al. |
| 5,540,713 A | 7/1996 | Schnepp-Pesch et al. |
| 5,545,211 A | 8/1996 | An et al. |
| 5,549,662 A | 8/1996 | Fordenbacher |
| 5,554,181 A | 9/1996 | Das |
| 5,556,413 A | 9/1996 | Lam |
| 5,562,697 A | 10/1996 | Christiansen |
| 5,707,387 A | 1/1998 | Wijay |
| 5,993,482 A * | 11/1999 | Chuter .......................... 623/1 |
| 6,039,756 A * | 3/2000 | Jang ............................. 623/1 |

* cited by examiner

STENT WITH NESTED OR OVERLAPPING RINGS

FIELD OF THE INVENTION

The field of this invention relates to vascular stents.

BACKGROUND OF THE INVENTION

Vascular stents are structures that are designed to maintain the patency of a vessel in the body. The stent provides internal support to allow the circulation to proceed therethrough. Stents can be used in the vascular system in ureters, bile ducts, esophagus, and in many other tubular structures in the human body.

Stents can be tubular or can be made from wire. Stents are typically made from a metal or polymeric substance or a metal coated with polymers which are biocompatible or contain heparin to reduce blood clotting or other tissue reactions. Many prior designs have used a coil approach where a wire is helically wound on a mandrel. Yet other designs have evolved—braided wire mesh and angulated wire forms wrapped on a spindle to form a coil.

U.S. Pat. No. 5,292,331 by Boneau and U.S. Pat. No. 5,403,341 describe such wire forms. These devices have very poor radial support to withstand the hoop strengths of the artery or vein and further are not suitable for arteries that are bent or curved or for long lesions; multiple stent are required. These designs do not provide any support to hold the wall of the artery, other than the memory of the metal.

Wall Stent, produced by Pfizer Inc., is a braided wire tube. Although this stent is flexible so as to be placed in curved arteries or veins and other body cavities, it does not have any radial strength imparted to it by design.

Wiktor, Pat. Nos. 4,649,922; 4,886,062; 4,969,458; and 5,133,732 describe a wire form stent. He describes stents made of wire helix made of a preformed wire which is in the sinusoidal form, in which either all or some of the adjacent strands are connected.

Arthus Fontaine, Pat. No. 5,370,683, also describes a similar device where a flat wire form of sinusoidal shape is wound on a mandrel to form a helical coil, the wire bends are "U" shaped and are connected to alternate "U"-shaped bands.

Allen Tower, U.S. Pat. Nos. 5,217,483 and 5,389,106 describes a similar device where the wire is preformed to a sinusoidal shape and subsequently wound on a mandrel to form a helical coil.

All of the above-described art fails to provide radial support. The preshaped wire form (sinusoidal in most of the prior art) is wrapped on a mandrel to form a coil. However, the forces imported by the vessel wall's hoop strength are radially inward. In other words, the force is acting perpendicular to the plane of the U-shaped wire form. This means that the bends that are in the wire add no structural strength to the wire form to support the force produced by the wall, which is radially inward.

When we examine the simple coils, such as taught in U.S. Pat. Nos. Scott 5,383,928 or Gene Samson 5,370,691 or Rolando Gills 5,222,969, it is apparent that the spring coil will withstand substantial radial forces due to the vessel wall; however, all these stents are bulky in their pre-expanded form and are hard to place in small and curved arteries or veins of the body. Also, a major disadvantage of this design is that when the coil stent is placed in a curved artery or vein, it forms an "accordion" shape whereby some strands in the outer radius are spread and those of the inner radius are gathered. Spring coils can also "flip" to form a flat structure when a longitudinal force is applied on one side of the stent.

The other types of stents that have been developed are tube stents. Palmer, U.S. Pat. Nos. 4,733,665; 4,739,762; 7,776,337; and 4,793,348 describe such a tube stent of slotted metal tube. The slotted metal tube is expanded by a high-pressure balloon to implant the stent into the inside wall of the artery or vein.

Joseph Weinstein, U.S. Pat. No. 5,213,561 describes a similar stent made of tubular materials with slots cut into it. On expansion using a balloon, it forms a structure with diamond-shaped slots.

Henry Wall, U.S. Pat. No. 5,266,073 also describes a stent, tubular, that has slots machined into it. When expanded, the edges of the stent lock to form a cylinder. Not only is this device stiff and can only be used for short lesions, but also the diameter cannot be adjusted to meet the exact needs of the particular vessel but it is fixed to the predetermined sizes.

Lau and Hastigan, U.S. Pat. No. 5,344,426 describes a slotted tubular stent that has a structure similar to Henry Wall's but has provided prongs that will lock in as the stent is expanded.

Michael Marin, U.S. Pat. No. 5,397,355 also describes a tubular slotted stent with locking prongs.

All the above-described tube stents, although typically providing substantial radial support when expanded, are not flexible enough to be placed in curved vessels. Arteries and veins in the human body are mostly curved and are tapered. As such, these tube stents suffer from this main disadvantage.

European patent document 042172982 employs wires that are doubled up and whose ends are snipped off to make a given joint. Such doubling up at the junction of two elements with snipped off free ends creates a potential puncture problem upon radial expansion. The sheer bulk of the doubled up wires makes them rotate radially outwardly away from the longitudinal centerline of the stent, while the plain ends on such an arrangement which are snipped off offer the potential of sharp points which can puncture or damage the intima. On the other hand, the apparatus of the present invention, employing sharp angles, as defined, avoids this problem in an embodiment which illustrates a continuous wire or wire-like member bent into a sharp angle. This type of structure alleviates the concerns of sharp edges, as well as the tendency of a doubled up heavy joint to rotate outwardly toward the intima upon radial expansion of the stem, as would be expected in the EPO reference 042172982.

Often these stents are layered with polymeric sheaths that are impregnated with biocompatible substances or can be coated with heparin or hydrogel. Most sheath-type coatings reduce endothelial cell growth through the stent, which is a major requirement in successful stenting of body cavities such as arteries and veins.

One of the problems with prior designs of slotted tube and wire stents is that in their expanded state, the openings in them become fairly large. This allows tissue to protrude through these openings or windows. When there are protrusions into the body cavity through the stent, it causes disturbances to the blood flow, causing activation of platelets causing blood clotting. This phenomenon can also enhance the process of restenosis due to the large area exposed for neointimal formation.

FIG. 1 depicts two rings of a stent of a design known in the prior art. Rings 10 and 12 are each sinusoidal, having respective peaks 14 and 16 joined together by crossties such as 18. Respective valleys 20 and 22 are deposed opposite each other to create a lengthy elongated opening 24, which has a length 26 nearly as long as the distance from opposing valleys 20 and 22. FIG. 2 illustrates what happens to the oblong openings 24 when the rings 10 and 12 are expanded radially to set the stent of the prior art shown in FIG. 1. As shown in FIG. 2, each of the openings 24 is quite large, allowing tissue growth to enter therethrough, as shown in FIG. 3, which shows more rings than the rings 10 and 12 illustrated in FIG. 1. The tissue growth 28 significantly constricts the blood flow passage through the stent of the prior art shown in FIGS. 1–3.

One of the objectives of the present invention is to provide a stent which overcomes this problem. Alternative solutions are illustrated to achieve the objective of making the opening smaller to provide better resistance to tissue growth into the blood flow passage through the stent. Thus, in one embodiment, the objective is accomplished by nesting adjacent rings which have sinusoidal bending so as to more closely pack them to reduce the opening sizes between them. In yet another embodiment, adjacent sinusoidal rings are made to be overlapping to again accomplish the objective of deceasing opening sizes in the expanded state for a stent of a given diameter and length. These and other objectives will be readily apparent to those skilled in the art from a description of the preferred embodiments of the invention below.

SUMMARY OF THE INVENTION

A flexible stent is disclosed which reduced openings between rings by two alternative techniques. In the first instance, adjacent sinusoidally bending rings are nested to compact them closer together to reduce the opening sizes therebetween. In another embodiment, adjacent sinusoidal rings overlap each other to achieve the same effect. The assembly can be covered with a graft as a support therefor.

DETAILED DESCRIPTION OF THE DRAWINGS

DETAILED DESCRIPTION OF THE PREFERRED EMBODIMENT

Figure 1:
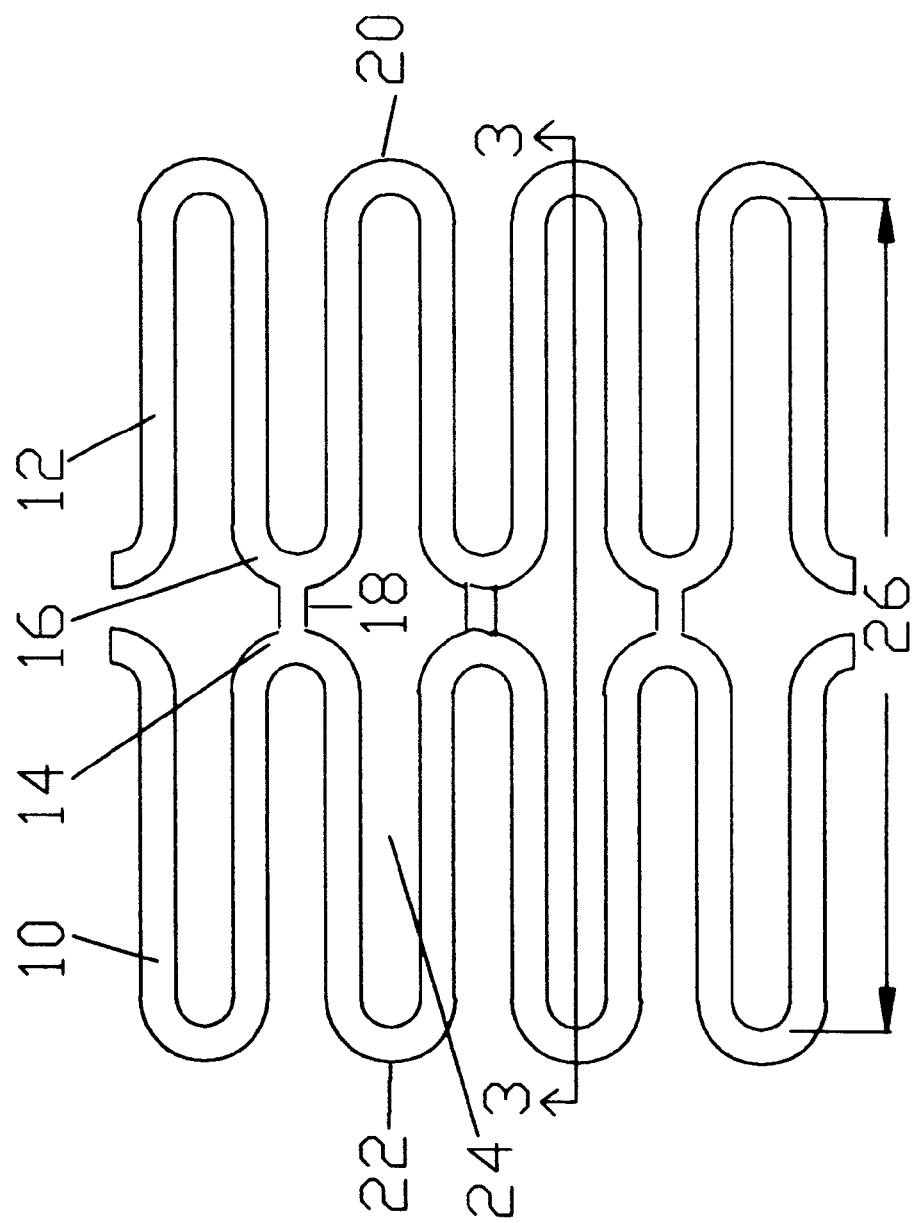
FIG. 1 is a partial flattened view of a stent of the prior art, showing sinusoidal rings with crossties connecting adjacent peaks.
Figure 2:
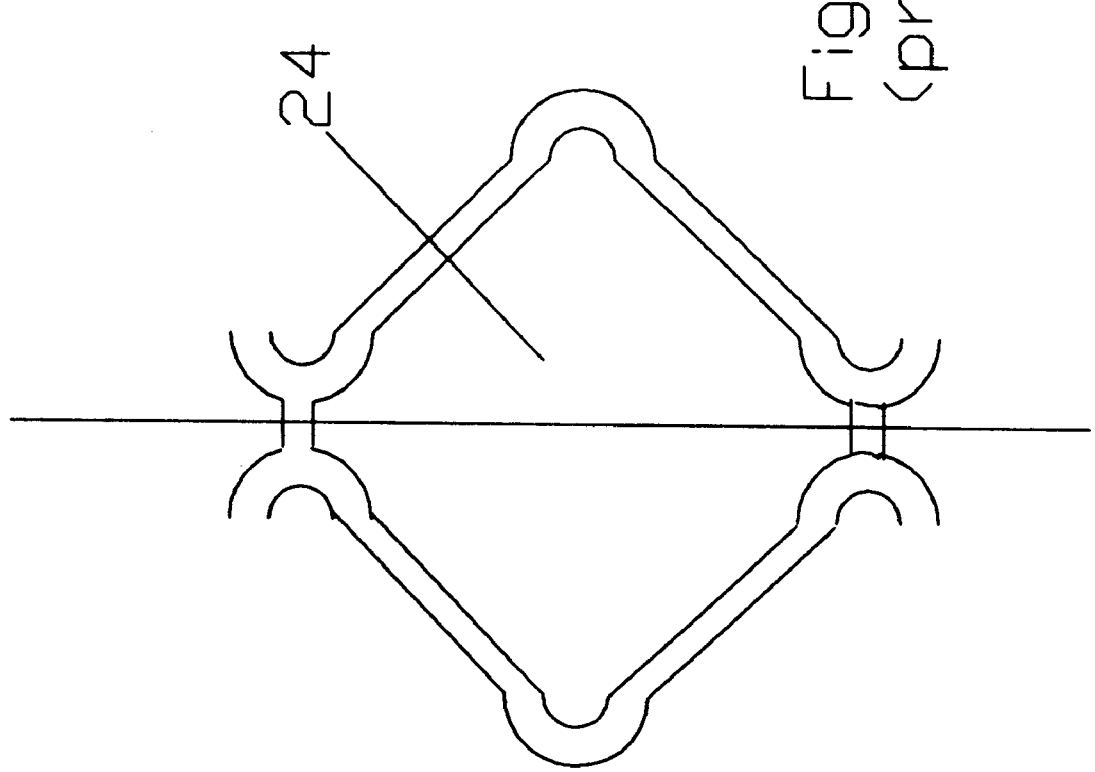
FIG. 2 is a view of one of the openings formed between adjacent rings in the prior art stent shown in FIG. 1.
Figure 4:
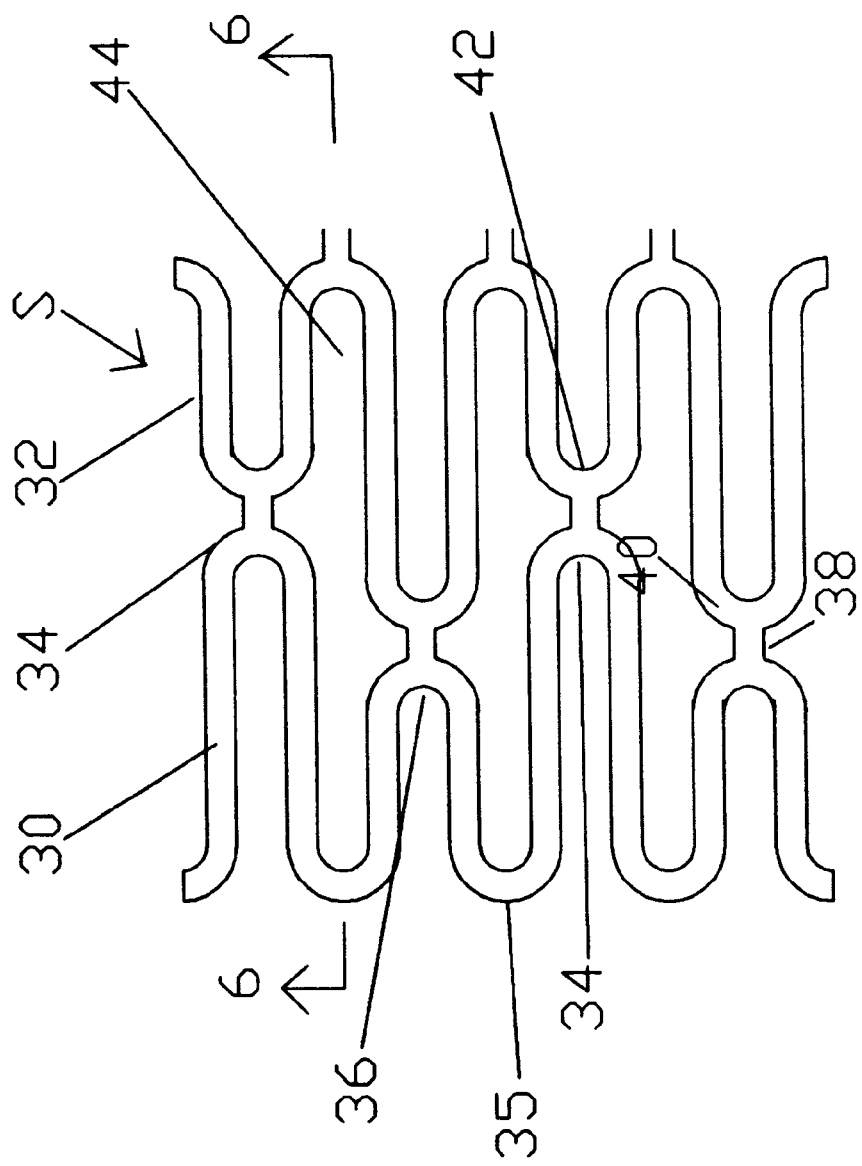
FIG. 4 illustrates two rings of a stent of one of the embodiments of the present invention shown in a flattened form.
Figure 5:
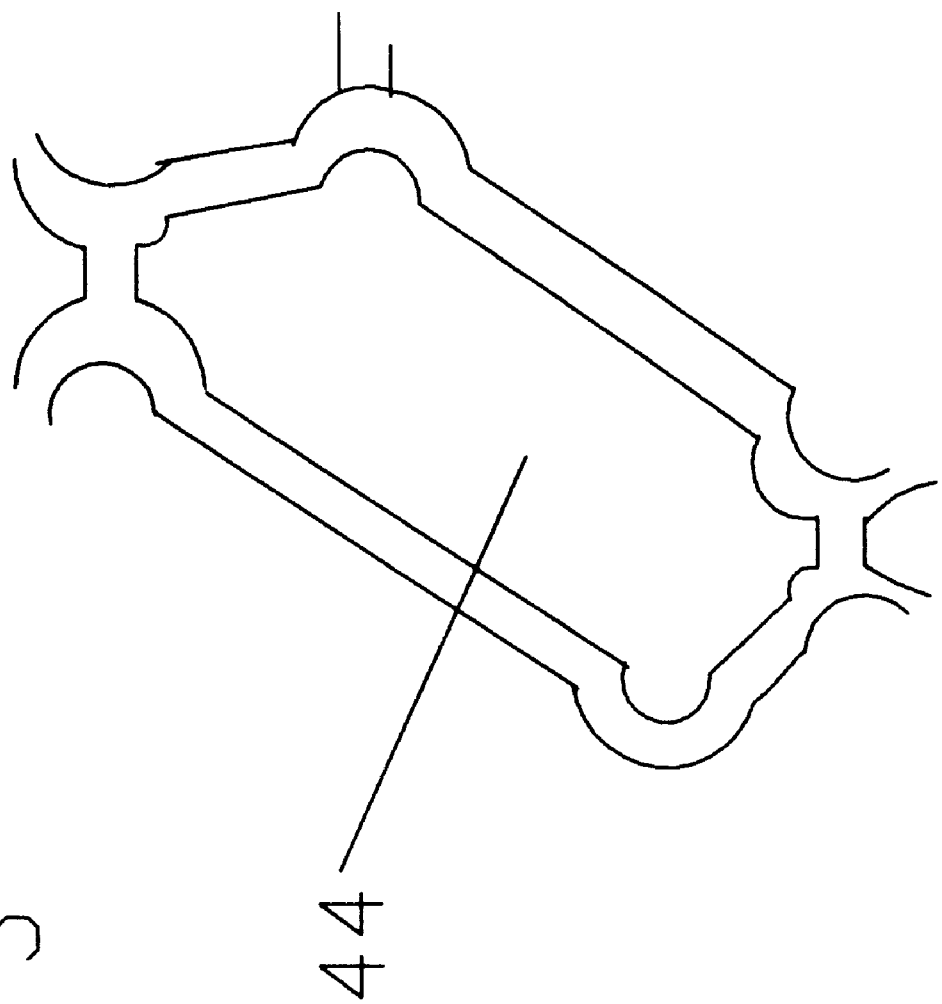
FIG. 5 illustrates one of the elongated openings of the stent of FIG. 4 after expansion.
Figure 7:
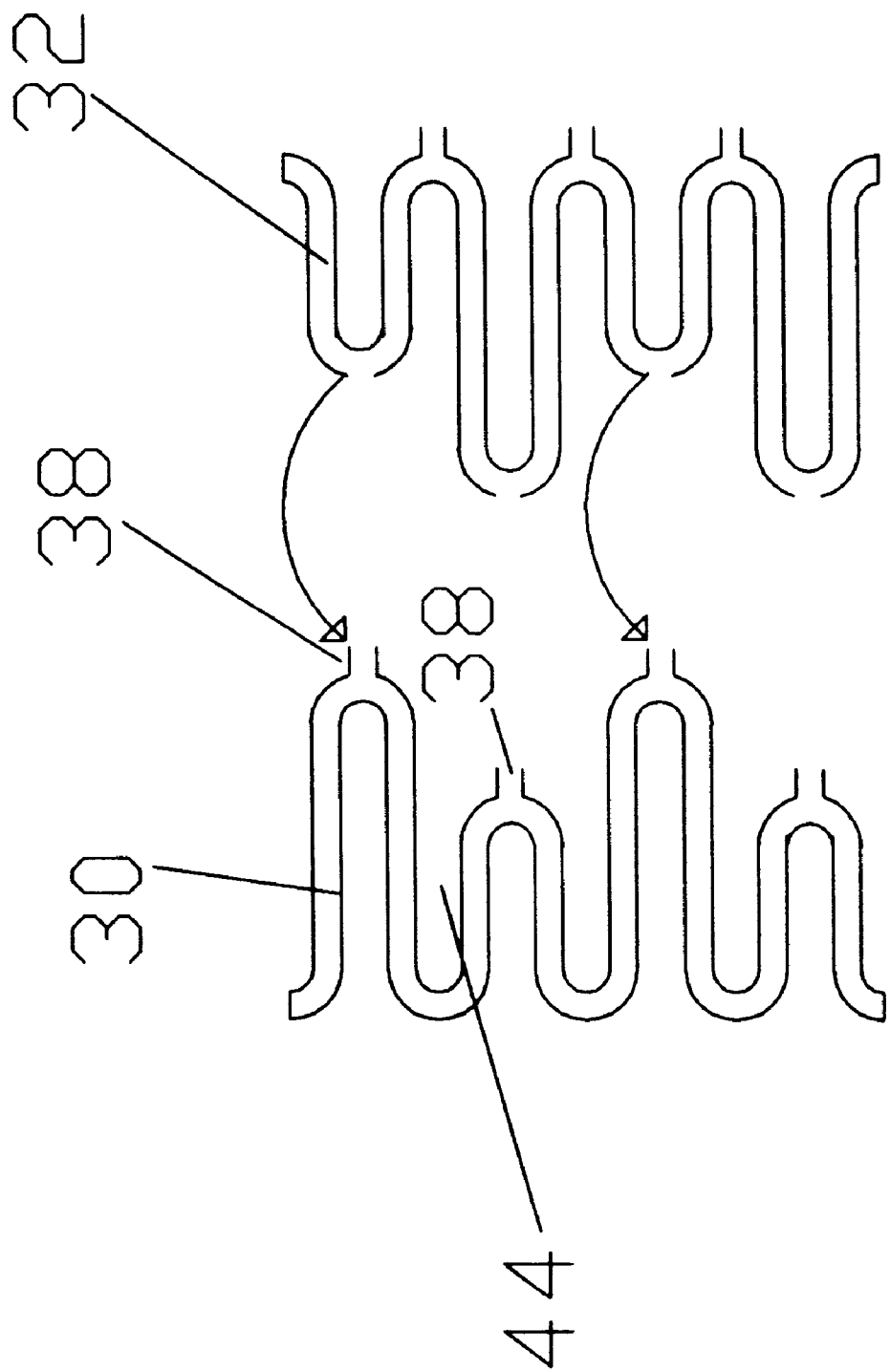
FIG. 7 shows how adjacent rings are connected to each other to form the stent of FIG. 4.
Figure 11:
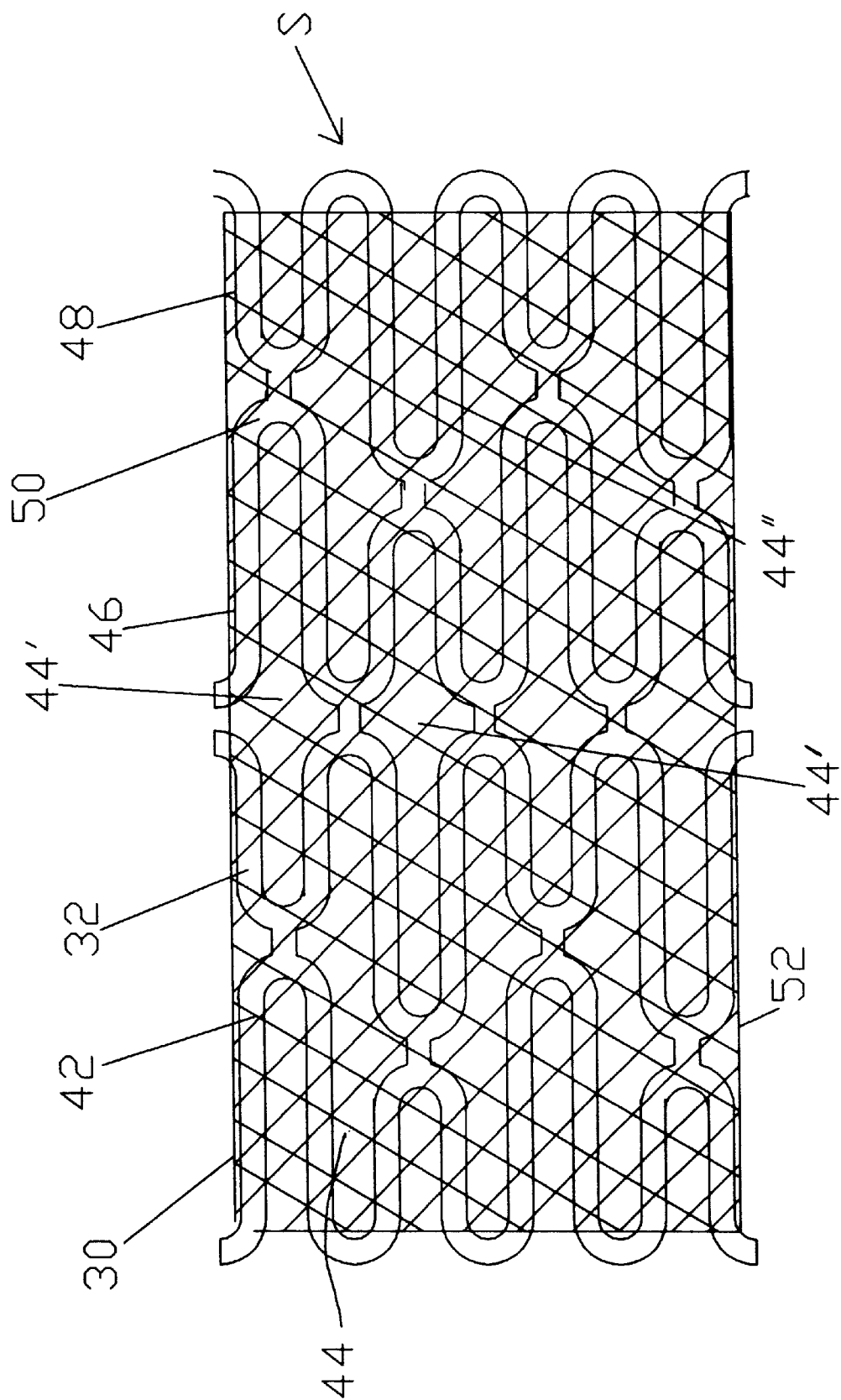
FIG. 11 is the stent of FIG. 4 with a graft around the outside.

Referring to FIG. 4, the preferred embodiment is illustrated. A portion of a stent S is shown in FIG. 4. More specifically, adjacent undulating rings 30 and 32 are illustrated. Each of these rings has an undulating, preferably sinusoidal shape with alternating high and low peaks. For example, in ring 30 alternating high peaks 34 exist between low peaks 36. Between peaks 34 and 36 are valleys 35. The height is defined as the distance from valleys 35 to peaks 34. The crossties 38 connect ring 30 to ring 32. Crossties 38 are optional as ring 30 can be connected directly to ring 32 without them. Crossties can connect peaks to peaks, valley to valley, or at least one peak or one valley to another location on the next ring. Ring 32 has alternating high peaks 40 and low peaks 42. The high peaks 40 of ring 32 are juxtaposed against the low peaks 36 of ring 30. Similarly, the low peaks 42 of ring 32 are juxtaposed against the high peaks 34 of ring 30. FIG. 5 illustrates the resultant shape of the opening 44 after radial expansion of the rings such as 30 and 32 which make up the stent S. FIG. 5 can be compared to FIG. 2 to illustrate that the typical opening in the stent S of the preferred embodiment of the present invention is smaller than the large oblong openings 24, which necessarily arise when rings such as 10 and 12 are aligned adjacent peak 14 to peak 16 with a crosstie 18 in between. In a sense, the rings 10 and 12 of the prior art get no closer to each other then the length of the crosstie 18 and there is no nesting or overlapping between rings 10 and 12 of the design in the prior art. Referring to FIG. 11, additional rings are shown besides rings 30 and 32. These rings 46 and 48 reflect a continuation of a pattern. As can be seen from FIG. 11, the peaks 50 of ring 46 extend in alignment but in the opposite direction from the low peaks 42 of ring 32 to create an opening 44' which is the same size as opening 44. In the embodiment shown in FIG. 11, a graft 52 is mounted over the stent S. Those skilled in the art will appreciate that, in the preferred embodiment, the openings 44 and 44' are identical and form a spiral pattern around the periphery of the stent S. The spiral pattern is continued with openings 44" which exist between rings 46 and 48. Those skilled in the art will appreciate that each ring does not need to be identical to its adjacent ring. It is within the scope of the invention that the greatest peak-to-valley height is varied from one ring to the next. The preferred embodiment is to make such height longer at ends of the stent and shorter in between. Also, the degree of nesting of adjacent rings such as 30 and 32 can be varied along with the width of openings such as 44 by adjusting the heights of the corresponding peaks and valleys. The prior art FIG. 1 depicts an extreme in the spacing between adjacent rings which provides the maximum width of openings 24. At the other extreme, adjacent rings such as 30 and 32 in effect become a single ring. The present invention is directed to the range of designs in between the two stated extremes which result in narrowing the longitudinal gap such as 44, 44', and 44", etc., while maintaining the rings such as 30, 32, 46, and 48 distinct and connected with crossties such as 38. The stent S of FIG. 11 is assembled in a technique shown in FIG. 7, which involves taking adjacent rings such as 30 and 32, aligning them as previously described, and welding the crossties 38 to join ring 30 to ring 32 in alternating locations. Each opening 44 is identified by a welded crosstie 38 above and below.

Figure 3:
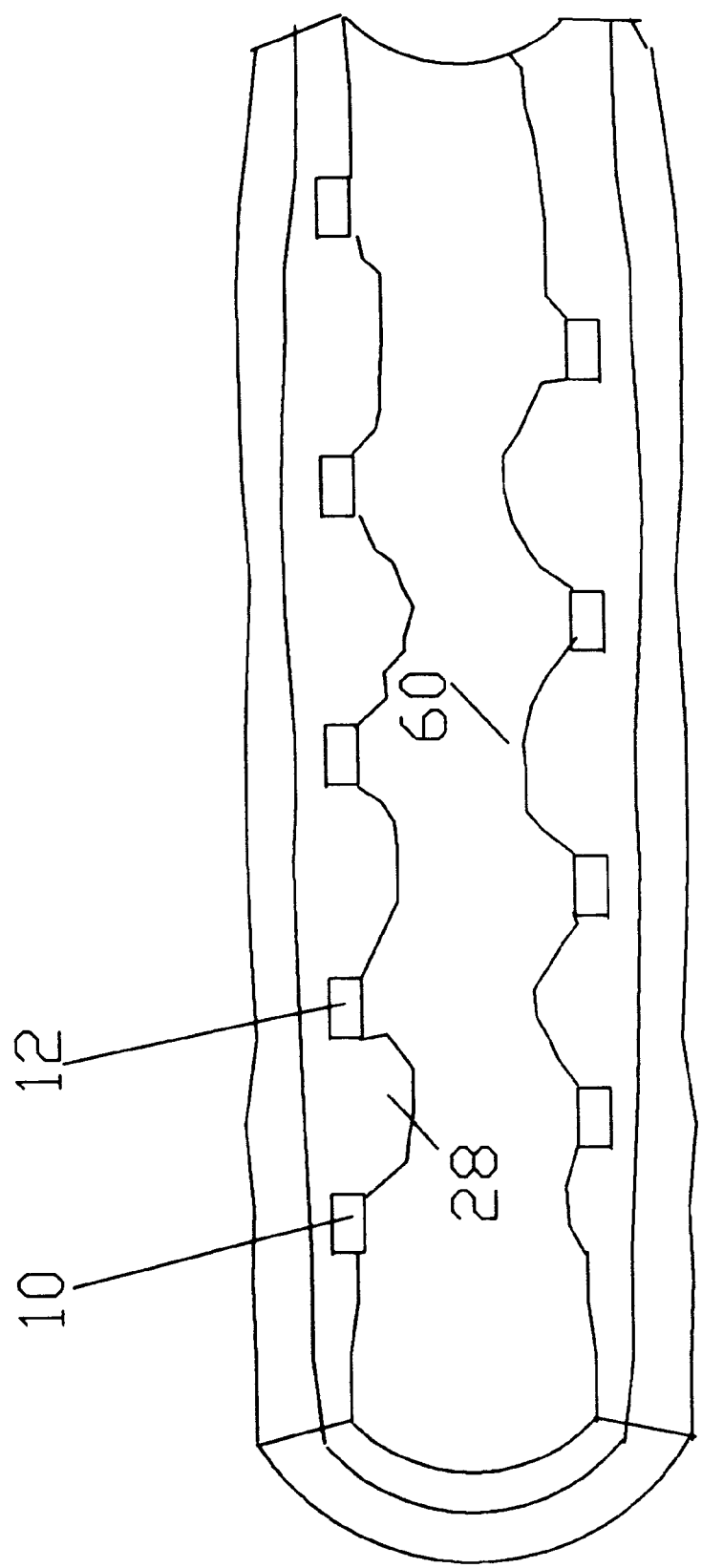
FIG. 3 is a section view through the stent shown in FIG. 1.
Figure 6:
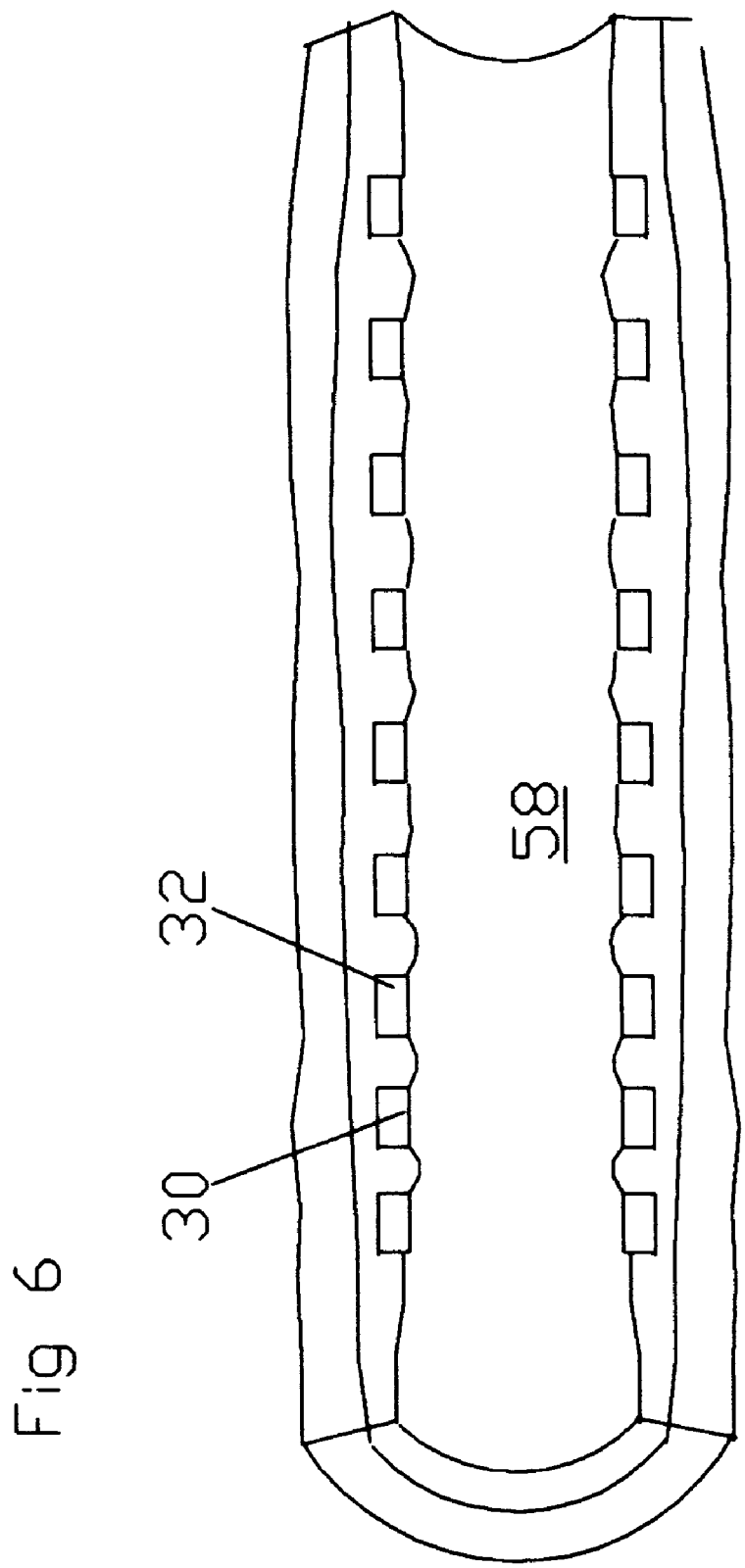
FIG. 6 is a section view of the stent of FIG. 4.

Accordingly, those skilled in the art can see that when the stent S of the preferred embodiment illustrated in FIG. 4 is inserted into a vessel as shown in FIG. 6, the gaps, such as between rings 30 and 32 which define the width of openings 44, are significantly smaller than the oblong openings 24 between rings 10 and 12 of the prior art as shown in FIG. 3. Thus, the central passage 58 is not obstructed by an invasion of tissue 28 in the design of FIG. 4, illustrated in section in FIG. 6. This should be contrasted to the constriction and internal roughness of the passage 60 as illustrated in FIG. 3.

Figure 9:
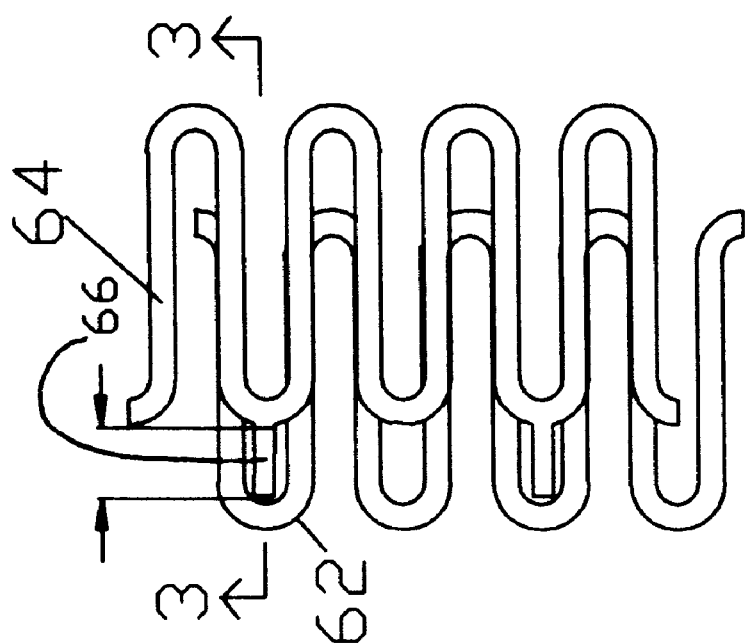
FIG. 9 shows the stent of FIG. 8 with two overlapping rings connected.
Figure 8:
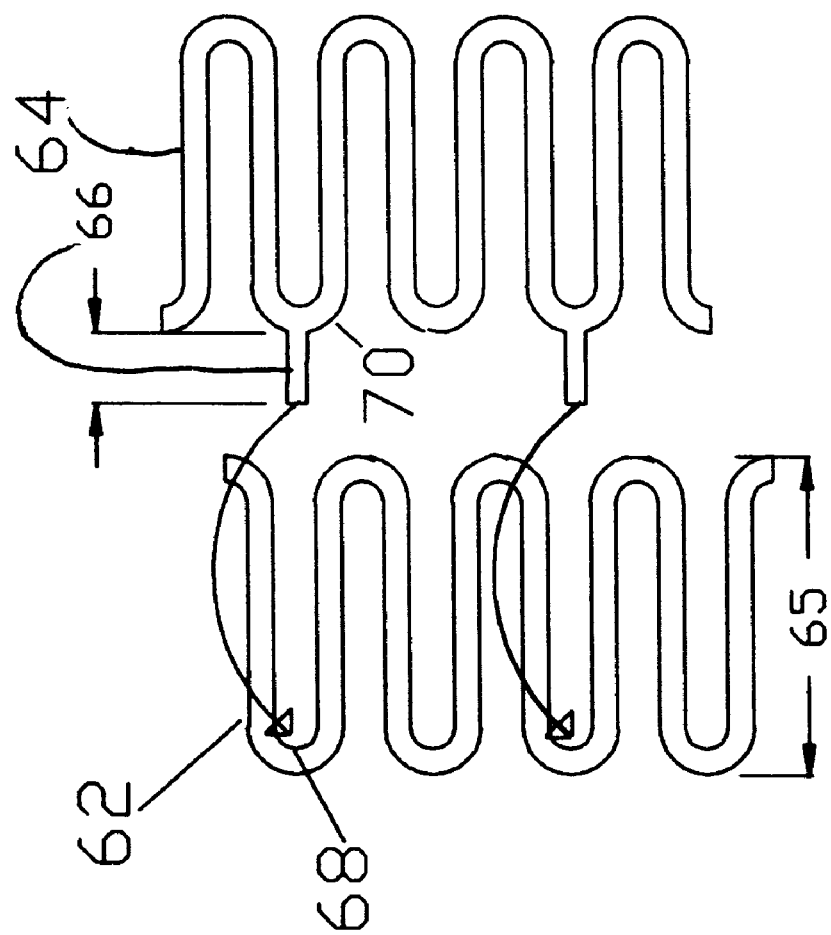
FIG. 8 shows an alternative embodiment to the stent of FIG. 4 and the technique for connecting adjacent rings.
Figure 10:
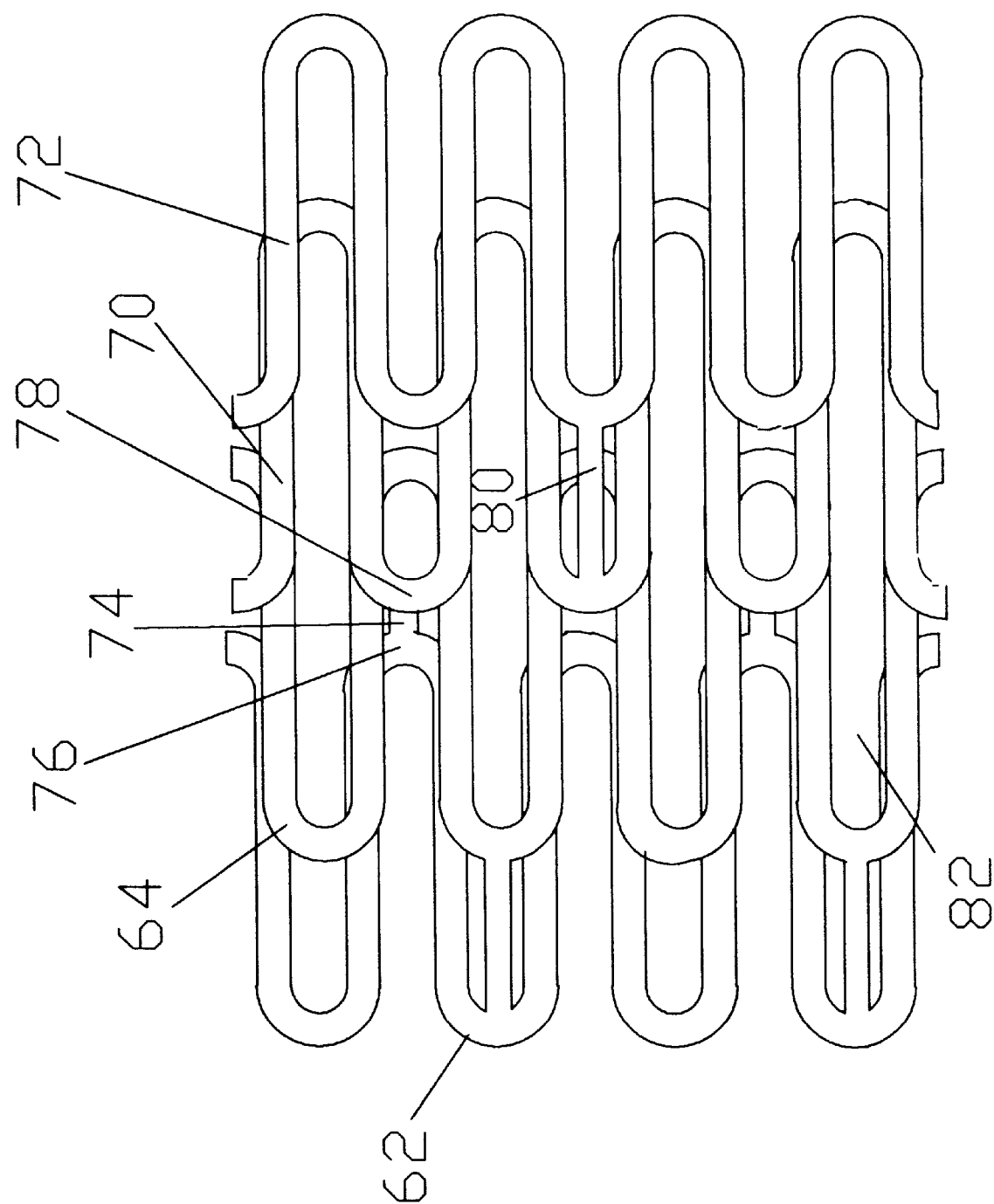
FIG. 10 is the stent of FIGS. 8 and 9 showing four overlapping rings.

Yet another embodiment of the present invention is shown in FIGS. 8 through 10. Here, adjacent rings 62 and 64 are built identically with an undulating, preferably sinusoidal shape, with each bend preferably having the same height 65 as the adjacent band akin to the individual rings 10 and 12 illustrated in the prior art. Varying heights can also be used. However, the method of connection of adjacent rings 62 and 64 is substantially different wherein the crossties 66 are connected to an opposing valley 68. Thus, for example, as shown in FIG. 8, the crossties 66 from a peak 70 connect to valley 68 of ring 62. The crossties can be connected to other locations. FIG. 9 illustrates the appearance of rings 62 and 64 after the crossties 66 are positioned for welding. As can readily be seen, the ring 64 overlaps ring 62. The amount of overlap can be varied with a variety of techniques, such as variation of the length of the crossties 66 or the peak-to-valley heights of either of the rings 62 or 64. FIG. 10 illustrates rings 62 and 64 with additional rings 70 and 72. As seen in FIG. 10, crossties 74 extend from ring 62 at its various peaks 76 to be connected to peaks 78 of ring 70. The crossties 74 literally extend between the undulations of ring 64 to reach the peak 78 of ring 70. Ring 72 is connected to ring 70 by crossties 80, putting ring 72 in an overlapping relationship with ring 70, while ring 70 overlaps ring 64 and, in turn, ring 64 overlaps ring 62. As shown in FIG. 10, it can be seen that a series of oblong openings of different sizes are provided. Openings 82 are the widest in this design and their width is affected by the configuration of the individual rings as well as the length of the crossties connecting them so that the width of opening 82 can be lengthened or shortened as desired. Those skilled in the art will appreciate that the smaller the width of opening 82, the stiffer the stent and the more difficult the stent can become to maneuver. The stent of FIG. 10 is generally stiffer than the stent of FIG. 4 in view of the fact that the rings 62, 64, 70, and 72 overlap each other, generally increasing the thickness of the stent being formed and somewhat decreasing its central passage when compared to a comparable design using the nesting technique shown in FIG. 4. The advantage of the design in FIG. 10 is that the size of the openings, particularly their width, can be more carefully controlled and reduced to present the stent with a smaller opening area so as to take maximum advantage of the smaller openings to obtain the desired effect shown in FIG. 6. Thus, either of the two designs can be used alternatively, depending on the application and the accessability to the location for setting the particular stent. The desirable advantage of either design is that the intrusion of tissue due to overly large openings, which present themselves after expansion in the designs of the prior art such as shown in FIG. 1, are dramatically reduced with either of the alternative designs illustrated.

The foregoing disclosure and description of the invention are illustrative and explanatory thereof, and various changes in the size, shape and materials, as well as in the details of the illustrated construction, may be made without departing from the spirit of the invention.

What is claimed is:

1. A stent, comprising:

a plurality of pairs of first and second rings, said first rings having an undulating form defining a first end and said second rings having an undulating form having a second end, said undulating form of said first rings defining said first end by alternating high and low peaks, and said undulating form of said second rings defining said second end by alternating high and low peaks;

said first and second ends are positioned facing each other with high peaks on said first end disposed in substantial longitudinal alignment with low peaks on said second end and low peaks on said first end disposed in substantial longitudinal alignment with high peaks on said second end, so as to allow said first and second rings to nest; and at least one connector to connect adjacent rings.

2. The stent of claim 1, wherein:

said high and low peaks on said first end define a plurality of first valleys therebetween;

said high and low peaks on said second end define a plurality of second valleys therebetween;

said first valleys are in substantial longitudinal alignment with said second valleys.

3. The stent of claim 1, wherein:

said connector comprises a crosstie extending from adjacent said high peak on said first end to adjacent said low peak on said second end.

4. The stent of claim 3, wherein:

said crosstie extends from a high peak on said first end to a low peak on said second end.

5. The stent of claim 4, further comprising:

said crosstie comprises a plurality of crossties disposed at each pair of longitudinally aligned peaks of said first and said second ends.

6. The stent of claim 1, wherein:

said connector comprises a direct connection of longitudinally aligned peaks from said first and second ends to each other.

7. The stent of claim 1, wherein:

said longitudinal alignmemt of said high peaks on said first end with said low peaks on said second end coincides with a longitudinal axis of said rings.

8. The stent of claim 1, further comprising:

a graft supported by said rings.

* * * * *